United States Patent [19]

Nakajima

[11] Patent Number: 4,853,540

[45] Date of Patent: * Aug. 1, 1989

[54] APPARATUS FOR RECORDING A RADIATION IMAGE OF AN OBJECT ON A STIMULABLE PHOSPHOR SHEET TO FACILITATE LATER RECONSTRUCTION OF AN ARBITRARY TOMOGRAPHIC IMAGE OF THE OBJECT

[75] Inventor: Nobuyoshi Nakajima, Kaisei, Japan

[73] Assignee: Fuji Photo Film Co., Ltd., Kanagawa, Japan

[ * ] Notice: The portion of the term of this patent subsequent to Aug. 9, 2005 has been disclaimed.

[21] Appl. No.: 870,952

[22] Filed: Jun. 5, 1986

[30] Foreign Application Priority Data

Jun. 5, 1985 [JP] Japan ................ 60-121656

[51] Int. Cl.⁴ .................................... G01T 23/04
[52] U.S. Cl. ............................ 250/327.2; 378/21; 378/22; 378/23; 378/27
[58] Field of Search ................ 378/23, 27, 22, 21; 250/327.2, 484.1

[56] References Cited

U.S. PATENT DOCUMENTS

| | | | |
|---|---|---|---|
| 3,499,146 | 3/1970 | Richards | 378/23 |
| 4,258,264 | 3/1981 | Kotera et al. | 250/484.1 |
| 4,276,473 | 6/1981 | Kato et al. | 250/327.2 |
| 4,315,318 | 2/1982 | Kato et al. | 364/515 |
| 4,346,295 | 8/1982 | Tanaka et al. | 250/327.2 |
| 4,387,428 | 6/1983 | Ishida et al. | 364/414 |
| 4,581,535 | 4/1986 | Komaki et al. | 250/327.2 |
| 4,641,242 | 2/1987 | Kimura | 364/414 |

FOREIGN PATENT DOCUMENTS

| | | | |
|---|---|---|---|
| 0114978 | 8/1984 | European Pat. Off. | 250/327.2 |
| 0028889 | 3/1977 | Japan | 378/27 |
| 0011395 | 2/1981 | Japan | 250/327.2 |
| 0241615 | 4/1969 | U.S.S.R. | 378/27 |

*Primary Examiner*—Janice A. Howell
*Assistant Examiner*—Constantine Hannaher
*Attorney, Agent, or Firm*—Gerald J. Ferguson, Jr.

[57] ABSTRACT

A radiation image recording apparatus comprises a radiation source for emitting a radiation to an object, a device for moving the radiation source to change the irradiation angle, a sheet changer for feeding a stimulable phosphor sheet to an image recording position exposed to the radiation passing through the object to have a radiation image of the object stored on the stimulable phosphor sheet and then receiving a drive signal to remove the stimulable phosphor sheet from the image recording position and feed a next stimulable phosphor sheet thereto, and a device for moving the sheet changer so that the stimulable phosphor sheet at the image recording position and the radiation source satisfy the linear rule and the geometric rule with respect to a point within the object or in the vicinity thereof. A controller controls operations of the devices for moving the sheet changer and the radiation source, intermittently activates the radiation source to emit the radiation at different irradiation angles, and sends the drive signal to the sheet changer after the radiation source is activated.

4 Claims, 4 Drawing Sheets

APPARATUS FOR RECORDING A RADIATION IMAGE OF AN OBJECT ON A STIMULABLE PHOSPHOR SHEET TO FACILITATE LATER RECONSTRUCTION OF AN ARBITRARY TOMOGRAPHIC IMAGE OF THE OBJECT

BACKGROUND OF THE INVENTION

1. Field of the Invention

This invention relates to a radiation image recording apparatus for recording a radiation image of an object. This invention particularly relates to a radiation image recording apparatus for recording a radiation image of an object on a stimulable phosphor sheet for storing radiation energy so that an arbitrary tomographic image of the object may later be reconstructed.

2. Description of the Prior Art

As a method of obtaining a tomographic image of a desired tomographic layer of an object such as the human body, tomography has heretofore been known. In tomography, a radiation source such as an X-ray tube and a radiographic film are positioned with the object intervening therebetween and moved relative to each other at the time of exposure to a radiation around an arbitrary tomographic layer of the object so that the linear rule (specifying that the focal point of the radiation source, a point on the tomographic layer and a point on the radiographic film are positioned in a straight line) and the geometric rule (specifying that the ratio of the distance between the focal point of the radiation source and the tomographic layer to the distance between the tomographic layer and the radiographic film is maintained constant) are satisfied. In this manner, only an image of a desired tomographic layer is formed on the radiographic film, and images of the other tomographic layers of the object are blurred. As a result, a radiation image of only the desired tomographic layer of the object is obtained. In the tomography, it is only necessary that the linear rule and the geometric rule are satisfied, and movements of the radiation source and the radiographic film may be conducted along any path, for example, a linear path, a circular path, an elliptic path or a spiral path.

However, in the aforesaid tomography, only the tomographic image of a single tomographic layer of the object may be recorded by a single radiation image recording step. Accordingly, an attempt has been made to record radiation images of an object respectively on a plurality of radiographic films by emitting a radiation to the object in different directions, and integrating image signals detected from the radiographic films, thereby reconstructing a tomographic image of an arbitrary tomographic layer of the object. This method is called tomosynthetic reconstruction. The basic principle of this method will hereinbelow be described with reference to FIGS. 4A and 4B. As shown in FIG. 4A, a radiation source 10 constituted by an X-ray tube or the like is sequentially moved to positions R1, R2 and R3 while facing an object 11. A radiation 12 is emitted by the radiation source 10 to the object 11 at the respective positions R1, R2 and R3, and radiation images of the object 11 are respectively recorded on radiographic films F1, F2 and F3. During this operation, the radiation source 10 and each of the radiographic films F1, F2 and F3 are positioned to satisfy the linear rule and the geometric rule with respect to a point O within the object 11 or in the vicinity thereof. Therefore, images of the point O and an arbitrary point P within the object 11 are recorded on the radiographic films F1, F2 and F3 at positions as shown in FIG. 4B. Namely, the image of the point O is recorded at the same positions on the films F1, F2 and F3. On the other hand, the image of the point P spaced from the point O is recorded at different positions on the films F1, F2 and F3. Specifically, the image of the point P is shifted by $\Delta s$ from the image of the point O on the film F1, coincides therewith on the film F2, and is shifted by $-\Delta s$ therefrom on the film F3.

Accordingly, by shifting the image signals detected from the films F1 and F3 respectively by $\Delta s$ and $-\Delta s$ and integrating the shifted image signals with the image signal detected from the film F2, it is possible to obtain an image signal for reconstructing the image of only the tomographic layer T on which the point P lies. The shift value $\Delta s$ is given as a function of an irradiation angle $\theta$ of the radiation 12 with respect to the object 11. Though on the drawing sheet in FIG. 4A the radiation source 10 is shown as moved along a circular arc path, it may also be moved along a circular path normal to the drawing sheet in FIG. 4A while at the same time the radiographic films F1, F2 and F3 are moved along a circular path normal to the drawing sheet. In this case, the image of the point P is shifted two-dimensionally with respect to the image of the point O on the films F1, F2 and F3. Therefore, the image signals detected from the films F1 and F3 should be two-dimensionally shifted in the aforesaid integration.

However, in the aforesaid conventional method of reconstructing a tomographic image, radiation images are recorded on radiographic films. Therefore, it is necessary to detect the images on the radiographic films by use of a photometer or the like and to obtain the image signal for reconstruction of a tomographic image. This operation is very troublesome. In order to eliminate the troublesome operation, an attempt has been made to use an image intensifier (I.I.) as the radiation detector instead of the radiographic film, to record the radiation image formed on the I.I. by use of a television camera, and to obtain an image signal. However, with this method, resolution of the reconstructed tomographic image is low, and distortion becomes large.

SUMMARY OF THE INVENTION

The primary object of the present invention is to provide a radiation image recording apparatus suitable for reconstructing a tomographic image of an arbitrary tomographic layer of an object by a simple operation.

Another object of the present invention is to provide a radiation image recording apparatus suitable for quickly reconstructing a tomographic image of high image quality.

The present invention provides a radiation image recording apparatus comprising:

(i) a radiation source for emitting a radiation to an object, (ii) a radiation source movement means for moving said radiation source to change an irradiation angle of said radiation with respect to said object, (iii) a sheet changer for feeding a stimulable phosphor sheet to an image recording position exposed to said radiation passing through said object to have a radiation image of said object stored on said stimulable phosphor sheet at said image recording position, and thereafter receiving a drive signal to remove said stimulable phosphor sheet from said image recording position and feed a next stimulable phosphor sheet to said image recording position, (iv) a sheet changer movement means for moving said sheet changer so that said stimulable phosphor sheet at said image recording position and said radiation source approximately satisfy the linear rule and the geometric rule with respect to a point within said object or in the vicinity thereof, and (v) a controller for controlling operations of said sheet changer movement means and said radiation source movement means, intermittently activating said radiation source to emit said radiation at a plurality of positions where said irradiation angles are different, and sending said drive signal to said sheet changer after said radiation source is activated.

The "stimulable phosphor" referred to in this invention means a phosphor which is able to store radiation energy therein upon exposure to a radiation such as X-rays, $\alpha$-rays, $\beta$-rays, $\gamma$-rays, cathode rays, or ultraviolet rays, and then emit light in proportion to the stored energy of the radiation upon stimulation with stimulating rays such as visible light.

By "stimulable phosphor sheet" is meant a sheet-like recording material comprising the aforesaid stimulable phosphor. In general, the stimulable phosphor sheet is composed of a substrate and a stimulable phosphor layer overlaid on the substrate. The stimulable phosphor layer comprises an appropriate binder and the stimulable phosphor dispersed therein. When the stimulable phosphor layer is self-supporting, the stimulable phosphor layer can by itself form the stimulable phosphor sheet. The stimulable phosphor sheet is described in detail, for example, in U.S. Pat. Nos. 4,258,264, 4,276,473, 4,315,318 and 4,387,428, and Japanese Unexamined Patent Publication No. 56(1981)-11395. With the stimulable phosphor sheet, it is possible to record a radiation image at a higher sensitivity and a higher resolution with less distortion than with a radiographic film.

In the present invention, a plurality of stimulable phosphor sheets are respectively exposed to a radiation passing through an object at different irradiation angles by using the sheet changer to have a radiation image of the object stored thereon. The stimulable phosphor sheets are then respectively exposed to stimulating rays such as a visible light which cause the stimulable phosphor sheets to emit light in proportion to the stored radiation energy. The emitted light is photoelectrically detected to obtain an electric image signal representing the stored radiation image. By using the image signals thus obtained, it is possible to reconstruct a tomographic image.

In the radiation image recording apparatus of the present invention, since the radiation image of an object is directly detected as an electric signal and the radiation image is recorded on a stimulable phosphor sheet capable of recording the radiation image at a high resolution with less distortion, it is possible to reconstruct a tomographic image of an arbitrary tomographic layer of the object quickly and with a high image quality. Also, since the stimulable phosphor sheet exhibits a very high sensitivity, it is possible to decrease the radiation dose to the object. Further, since there is a sheet changer for quickly feeding a plurality of stimulable phosphor sheets sequentially to the image recording position, it becomes possible to record radiation images very quickly.

DESCRIPTION OF THE PREFERRED EMBODIMENTS

The present invention will hereinbelow be described in further detail with reference to the accompanying drawings.

Figure 1:
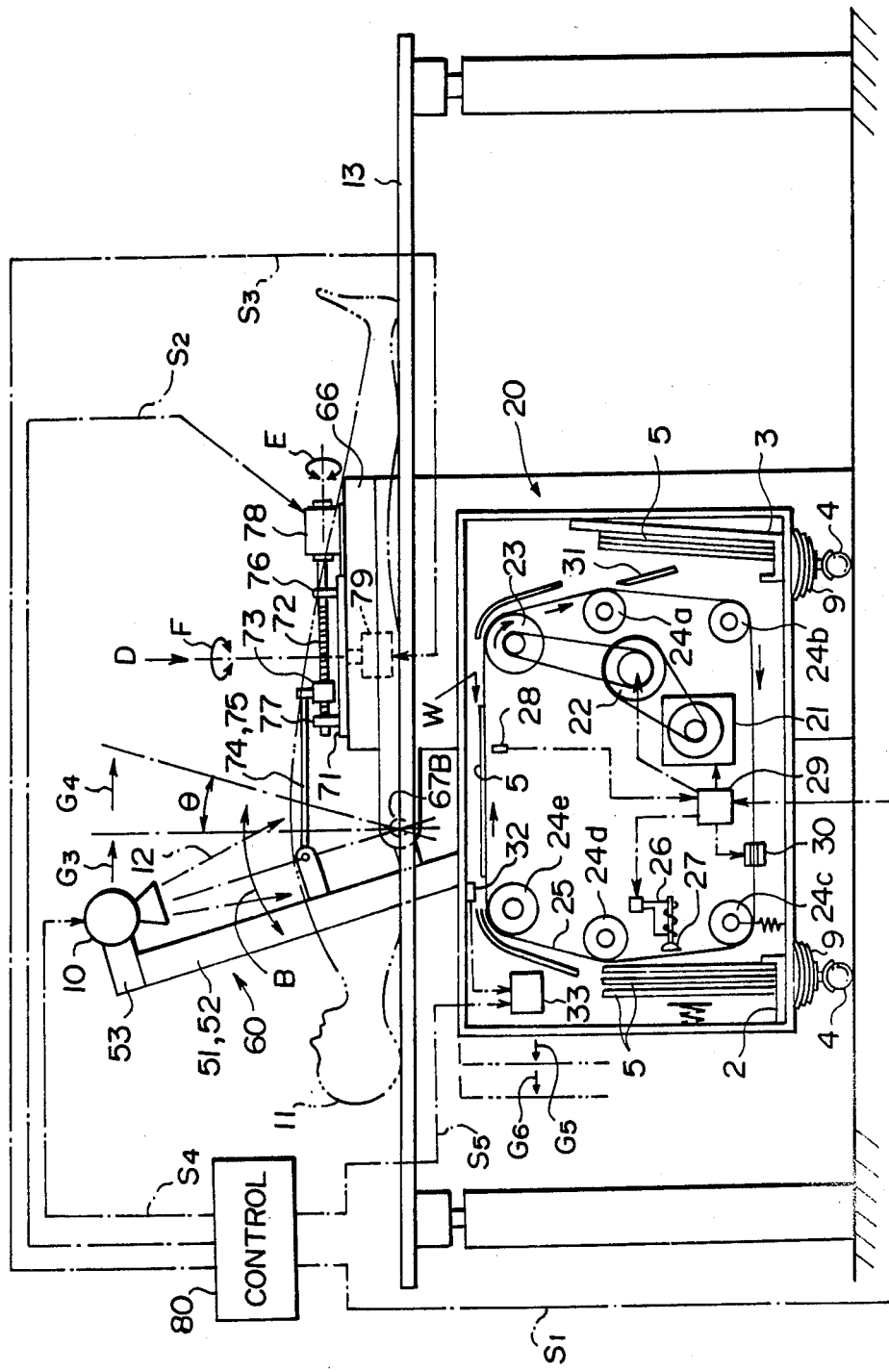
FIGS. 1 and 2 are a schematic elevational view and a side view showing an embodiment of the radiation image recording apparatus in accordance with the present invention.
Figure 2:
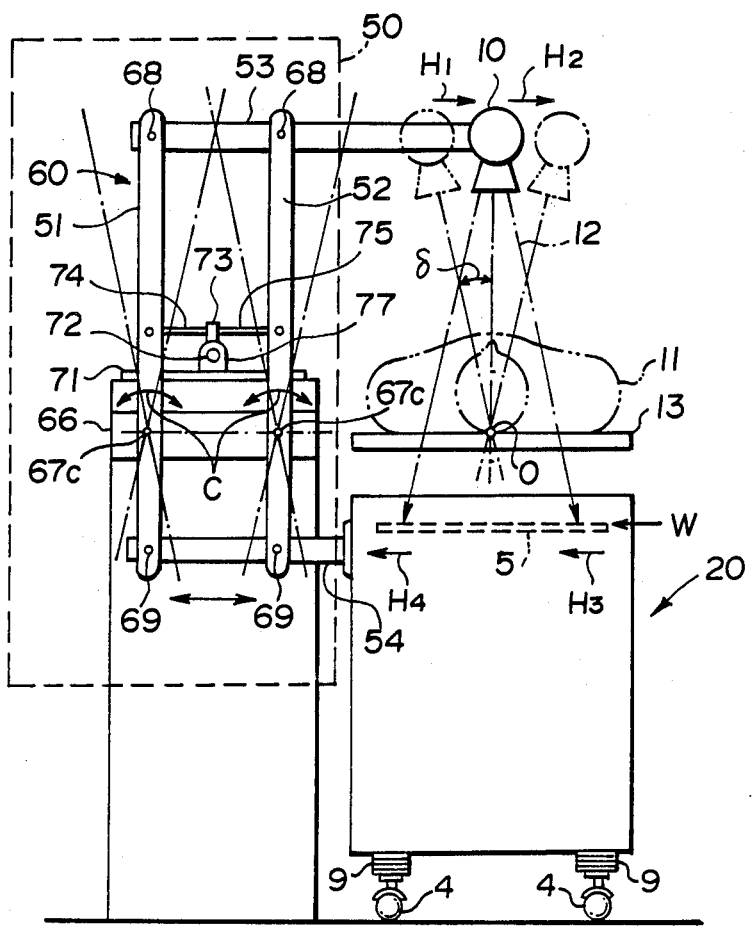

Referring to FIGS. 1 and 2, the radiation image recording apparatus comprises a radiation source 10 constituted by an X-ray tube or the like, an object supporting base 13 on which an object 11 lies, a sheet changer 20 for feeding a stimulable phosphor sheet 5 to an image recording position W exposed to a radiation 12 such as X-rays emitted by the radiation source 10 and passing through the object 11, a movement means 50 for moving the radiation source 10 so that the irradiation angle of the radiation 12 with respect to the object 11 changes and for moving the sheet changer 20, and a controller 80.

First, the sheet changer 20 will be described in detail. As shown in FIG. 1, the sheet changer 20 is provided with a first receiving section 2 for receiving unexposed stimulable phosphor sheets 5, a second receiving section 3 for receiving stimulable phosphor sheets exposed to the radiation 12, and a conveyance means for taking the stimulable phosphor sheets 5 one by one out of the first receiving section 2, quickly conveying the stimulable phosphor sheet 5 to the image recording position W, and quickly conveying the stimulable phosphor sheet 5 exposed to the radiation 12 to the second receiving section 3. At the first receiving section 2, a plurality of the stimulable phosphor sheets 5 are stored in a bare form or housed in cassettes each of which houses a single stimulable phosphor sheet. The sheet changer 20 can be moved backward and forward and to the right and left by means of the casters 4 provided on the bottom via leaf springs 9.

When radiation image recording is performed, a drive signal S1 is first sent from the controller 80 to a control section 29 in the apparatus, and the control section 29 activates a motor 21 upon receiving the drive signal S1 and puts a clutch 22 into engagement, and rotation of the motor 21 is thereby transmitted to a drive roller 23 via the clutch 22. An endless conveyor belt 25 mounted around the drive roller 23 and guide rollers 24a, 24b, 24c, 24d and 24e is moved in the direction indicated by the arrows when the drive roller 23 is rotated. A solenoid 26 is then energized by the control section 29 to move a pushing piece 27 leftwardly in FIG. 1 and bring the conveyor belt 25 into contact with the stimulable phosphor sheet 5 stored at the first receiving section 2. The conveyor belt 25 and the stimulable phosphor sheet 5 are constituted so that the sheet 5 is temporarily held by or adhered to the conveyor belt 25 by any means so that the sheet 5 may later be separated therefrom. For example, the conveyor belt 25 may be provided with engagement claws for engagement with engagement portions of the stimulable phosphor sheet 5, or may be provided with adhesive tape. Alternatively, the conveyor belt 25 may be provided with the male side of a face-to-face tape fastener and the sheet 5 with the female side of the face-to-face tape fastener, or vice versa. Or, the sheet 5 may be adhered to the conveyor belt 25 by magnetic attraction.

When the stimulable phosphor sheet 5 held by or adhered to the conveyor belt 25 is conveyed to the image recording position W, a sheet detection switch 28 detects the sheet 5 and sends a detection signal to the control section 29. Upon receiving the detection signal, the control section 29 disengages the clutch 22 and activates a brake 30 to stop the conveyor belt 25. In this manner, the stimulable phosphor sheet 5 is placed at the image recording position W facing the object 11.

The stimulable phosphor sheet 5 placed at the image recording position W is exposed to the radiation 12 passing through the object 11 as described later to have a radiation image of the object 11 stored on the sheet 5. Then, the drive signal S1 is sent from the controller 80 to the control section 29 in the apparatus to release the brake 30, to put the clutch 22 into disengagement, and to energize the solenoid 26. As a result, the stimulable phosphor sheet 5 carrying the radiation image stored thereon is removed from the image recording position W, separated from the conveyor belt 25 by a member 31 for releasing the holding or adhesion of the sheet 5 by the conveyor belt 25, and sent to the second receiving section 3. At the same time, the energized solenoid 26 activates the pushing piece 27, and the next stimulable phosphor sheet 5 is sent from the first receiving section 2 to the image recording position W and placed at the image recording position W in the same manner as described above.

In this embodiment, the stimulable phosphor sheets 5 are each provided with a bar code, and the bar code of the sheet 5 placed at the image recording position W is read by a bar code reader 32 and stored in a memory 33.

The sheet changer 20 and the radiation source 10 are connected by a connection means 60 constituting a part of the movement means 50. As shown in FIG. 2, the connection means 60 comprises vertical rods 51, 52 positioned in parallel with each other, a horizontal rod 53 carried on the upper end portions of the vertical rods 51, 52 by rotation shafts 68, and a horizontal rod 54 carried on the lower end portions of the vertical rods 51, 52 by rotation shafts 69. The radiation source 10 is supported by the horizontal rod 53, and the sheet changer 20 is supported by the horizontal rod 54. Further, the vertical rods 51 and 52 are supported on a base 66 at the center between the horizontal rods 53 and 54 so that the vertical rods 51 and 52 are rotatable around a shaft 67B in the direction as indicated by the arrow B as shown in FIG. 1 and rotatable around shafts 67C in the directions indicated by the arrows C in FIG. 2. The vertical rods 51 and 52 are connected to a drive means. As shown in FIGS. 1 and 2 and in FIG. 3 which is a plan view taken in the direction indicated by the arrow D of FIG. 1, the drive means comprises a rotatable table 71 positioned on the base 66, a male thread rod 72 positioned on the rotatable table 71, a female thread member 73 meshing with the male thread rod 72, and connection rods 74, 75 positioned in a triangular form with the base ends rotatably connected with the female thread member 73 and the opposite ends respectively connected with the vertical rods 51, 52. The male thread rod 72 is supported by bearings 76, 77 secured to the rotatable table 71 so that the male thread rod 72 may be rotated by a motor 78 in the direction indicated by the arrow E of FIG. 1. The rotatable table 71 is rotated by a motor 79 in the direction indicated by the arrow F. When the rotatable table 71 is rotated, the male thread rod 72 is rotated together with the rotatable table 71. However, since the base end of each of the connection rods 74 and 75 is rotatably connected with the female thread member 73, they do not obstruct rotation of the male thread rod 72.

Figure 3:
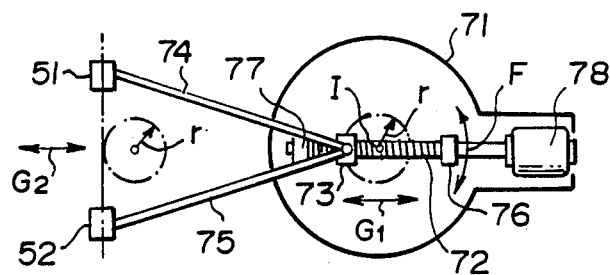
FIG. 3 is a plan view showing a part of the embodiment of FIG. 1, FIGS. 4A and 4B are explanatory views showing the method of reconstructing a tomographic image.
Figure 4A:
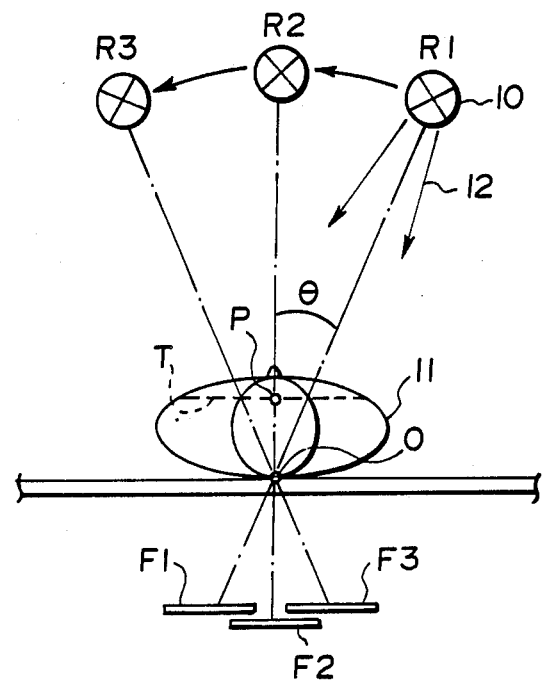
Figure 4B:
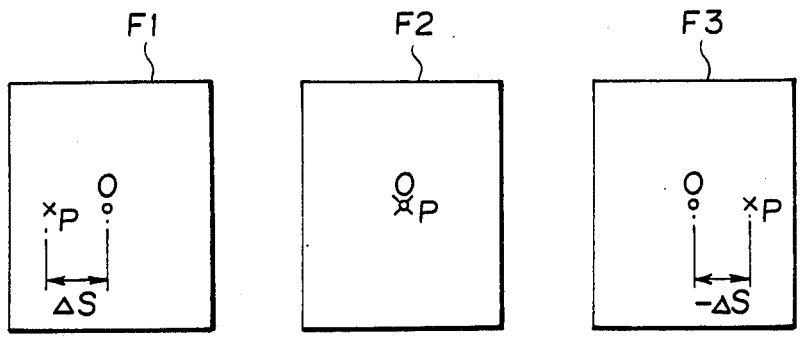

The triangular form defined by the vertical rods 51, 52, the female thread member 73, and the connection rods 74, 75 connecting them does not change. Accordingly, as shown in FIG. 3, when the rotatable table 71 is maintained still and the male thread rod 72 is rotated by the motor 78 to move the female thread member 73 linearly in the direction indicated by the arrow G1, the connection means 60 is also linearly moved in the direction indicated by the arrow G2. As a result, the radiation source 10 is moved, for example, in the directions indicated by the arrows G3 and G4 in FIG. 1, and the sheet changer 20 (and consequently the stimulable phosphor sheet 5 at the image recording position W) is moved in the directions indicated by the arrows G5 and G6. The aforesaid linear rule and the geometric rule hold with respect to a point on the extension of the shaft 67B between the radiation source 10 and the stimulable phosphor sheet 5. Also, when the same operation is conducted with the rotatable table 71 shown in FIG. 3 rotated by 90°, the radiation source 10 is moved in the directions indicated by the arrows H1 and H2 in FIG. 2, and the stimulable phosphor sheet 5 at the image recording position W of the sheet changer 20 is moved in the directions indicated by the arrows H3 and H4. Thus it is possible to conduct linear path image recording in these directions. In this case, too, the radiation source 10 and the stimulable phosphor sheet 5 moving relative to each other satisfy the linear rule and the geometric rule with respect to a point O on a plane on which the shafts 67C lie. Further, as shown in FIG. 3, when the female thread member 73 is deviated by a distance r from a rotation center I of the rotatable table 71 and the rotatable table 71 is rotated in this condition, the female thread member 73 moves along a circle having a radius r, and therefore, the connection means 60 moves along a circle having a radius r. In this manner, it is possible to carry out circular path image recording. Also, by combining the rotation of the male thread rod 72 in the direction indicated by the arrow E with the rotation of the rotatable table 71 in the direction indicated by the arrow F, it becomes possible to conduct radiation image recording along various paths, for example, along a spiral path. When the connection means 60 is moved in the direction indicated by the arrow G2, the vertical position of the horizontal rod 54 changes, and therefore, the sheet changer 20 moves vertically. However, the vertical movement of the sheet changer 20 is accommodated by resilient deformation of the leaf springs 9.

When radiation image recording is conducted for reconstructing an arbitrary tomographic image of the object 11, a first stimulable phosphor sheet 5 is sent to the image recording position W in the sheet changer 20. The controller 80 intermittently sends motor drive signals S2 and S3 respectively to drive circuits (not shown) for the motor 78 and 79 of the movement means 50, thereby intermittently operating the motors 78 and 79. The motor drive signals S2 and S3 are output in a pattern programmed for respective types of image recording, such as linear path image recording and circular path image recording. For example, for linear path image recording wherein the radiation source 10 is moved in the directions indicated by the arrows G3 and G4 in FIG. 1 and the sheet changer 20 (and consequently the stimulable phosphor sheet 5 at the image recording position W) is moved in the directions indicated by the arrows G5 and G6, only the drive signal S2 for operating the motor 78 is intermittently output. When output of the motor drive signal S2 or S3 is stopped, i.e. when the radiation source 10 and the sheet changer 20 are stopped, the controller 80 sends a drive signal S4 to the radiation source 10 to activate it. The radiation 12 is thus emitted by the radiation source 10 to the object 11, and a radiation image of the object 11 is stored on the stimulable phosphor sheet 5 at the image recording position W of the sheet changer 20 by the radiation 12 passing through the object 11. The controller 80 outputs the drive signal S4 as described above and outputs an irradiation angle signal S5 representing the irradiation angles of the radiation with respect to the object 11. The irradiation angle signal S5 is stored in the memory 33 of the sheet changer 20 in conformity with the bar code of the stimulable phosphor sheet 5 at the image recording position W. The irradiation angle signal S5 represents an irradiation angle $\theta$ in the direction shown in FIG. 1 and an irradiation angle $\delta$ in the direction shown in FIG. 2. The irradiation angles $\theta$ and $\delta$ correspond to the rotation amounts of the motors 78 and 79. Therefore, the irradiation angle signal S5 may be generated by integrating the motor drive signals S2 and S3 or based on the aforesaid program.

The controller 80 sends the drive signal S1 to the sheet changer 20 a minute time after the drive signal S4 is sent to the radiation source 10. In this manner, the stimulable phosphor sheet 5 carrying the radiation image stored thereon at the image recording position W is sent from the image recording position W the second receiving section 3, and the next stimulable phosphor sheet 5 is sent to the image recording position W. Then, the controller 80 outputs the motor drive signal S2 or S3 to move the radiation source 10 and the sheet changer 20 relative to each other based on the aforesaid program.

Figure 5:
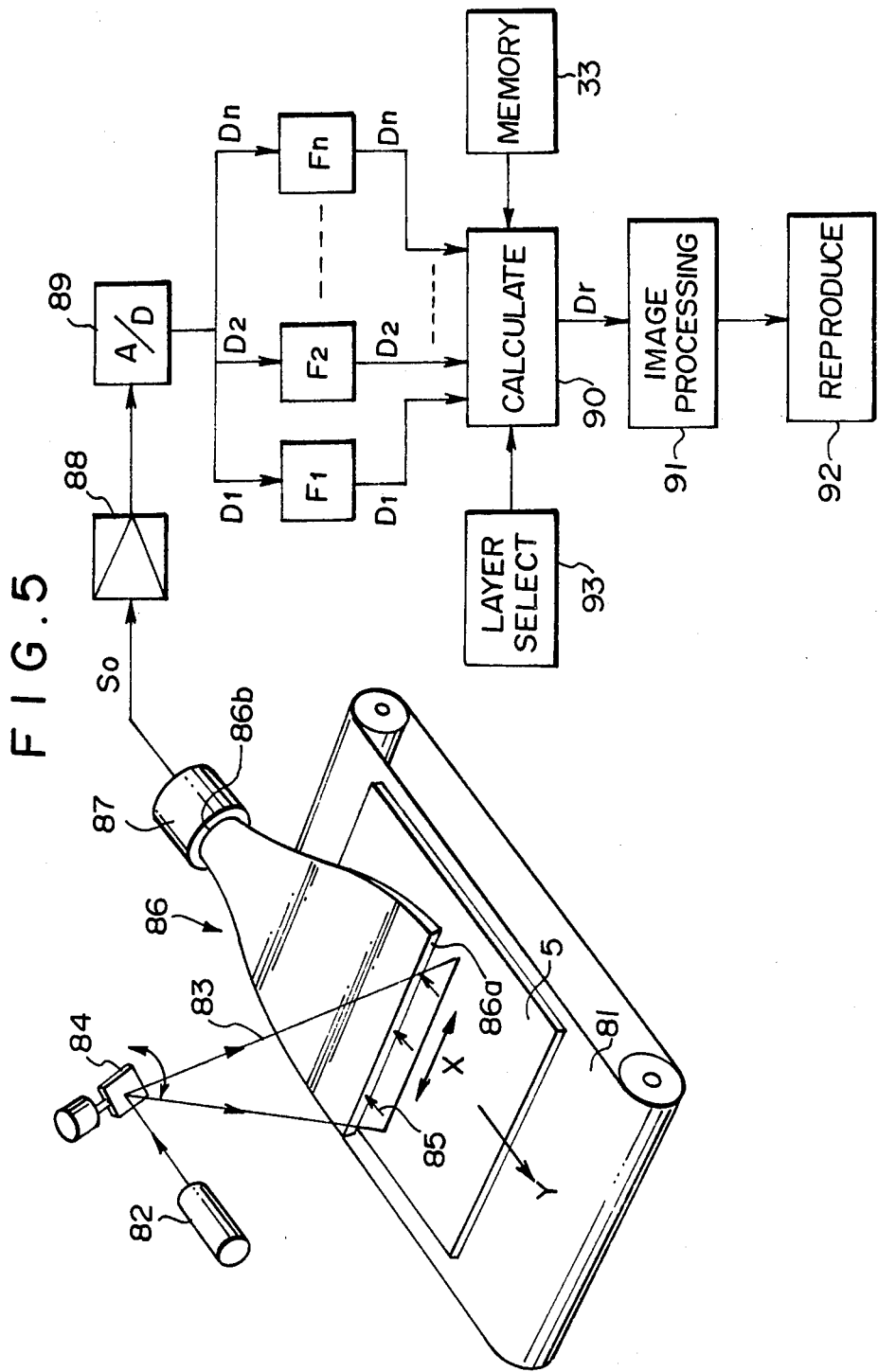
FIG. 5 is a schematic view showing an example of the system for reconstructing a tomographic image.

The aforesaid operation is repeated, and a radiation image of the object is recorded on a plurality of the stimulable phosphor sheets 5 by the radiation 12 irradiated at different irradiation angles $\theta$ and $\delta$. The stimulable phosphor sheets 5 carrying the radiation image stored thereon are taken out of the second receiving section 3 of the sheet changer 20, and subjected one by one to image read-out conducted with an apparatus shown in FIG. 5. In the image read-out, the stimulable phosphor sheet 5 is conveyed in the sub-scanning direction indicated by the arrow Y by a sheet conveyance means 81 which is constituted by an endless belt or the like. A laser beam 83 is emitted as stimulating rays by a laser beam source 82, and deflected by a light deflector 84 which may be a galvanometer mirror or the like to scan the stimulable phosphor sheet 5 in the main scanning direction indicated by the arrow X approximately normal to the sub-scanning direction indicated by the arrow Y. The portion of the sheet 5 exposed to the laser beam 83 emits light 85 in an amount proportional to the stored radiation energy. The emitted light 85 is guided inside of a light guide member 86 and photoelectrically detected by a photomultiplier 87 acting as a photodetector.

The light guide member 86 is fabricated by forming a light transmitting material such as an acrylic plate, and has a linear light input face 86a extending along a beam scanning line on the stimulable phosphor sheet 5 and a ringlike light output face 86b closely contacted with a light receiving face of the photomultiplier 87. The light 85 emitted by the stimulable phosphor sheet 5 and entering the light guide member 86 from its light input face 86a is guided inside of the light guide member 86 through total reflection up to the light output face 86b, and the amount of the emitted light 85 representing the radiation energy stored on the stimulable phosphor sheet 5 is detected by the photomultiplier 87. The light guide member 86 may be of a shape and a material as disclosed in U.S. Pat. No. 4,346,295, and may be made by a method described therein.

An output signal (read-out image signal) S0 of the photomultiplier 87 is amplified by a logarithmic amplifier 88 and digitized by an A/D converter 89. In this manner, a digital read-out image signal D1 representing the radiation image of the object 11 stored on the stimulable phosphor sheet 5 is obtained. The read-out image signal D1 is stored in an image file F1 which is constituted by a magnetic disk, an optical disk, a magnetic tape or the like. The bar code of the stimulable phosphor sheet 5 is also detected by the readout apparatus, and the bar code read-out signal is included in the read-out image signal D1.

The image read-out is also conducted for the other stimulable phosphor sheets 5 in the same manner as described above, and image signals D2, D3, . . . , Dn detected from the sheets 5 are respectively stored in image files F2, F3, . . . , Fn which may be of the same type as the image file F1.

Thereafter, a calculation apparatus 90 reads the image signals D1, D2, . . . , Dn from the image files F1, F2, Fn, integrates them after shifting them as described above, and generates an image signal Dr for reconstructing a tomographic image of a desired tomographic layer of the object 11. As described above, the shift value $\Delta s$ for each of the image signals D1, D2, . . . , Dn is given by a function $f(\theta, \delta)$ of the irradiation angles $\theta$ and $\delta$. Therefore, the calculation apparatus 90 identifies the bar code read-out signal included in each of the image signals D1, D2, . . . , Dn, reads the irradiation angles $\theta$ and $\delta$ corresponding to the identified bar code from the memory 33 of the sheet changer 20, and calculates the shift value $\Delta s$ based on the irradiation angles $\theta$ and $\delta$. The image signal Dr is sent to an image reproducing apparatus 92 via an image processing apparatus 91 for conducting gradation processing, frequency response processing or the like. The image reproducing apparatus 92 comprises a cathode ray tube (CRT), an optical scanning recording apparatus or the like, and displays the image represented by the image signal Dr, i.e. the tomographic image of the object 11, and reproduces the image as a hard copy. The calculation apparatus 90 changes the function $f(\theta, \delta)$ by the operation of a tomographic layer selecting knob 93. As a result, the shift values $\Delta s$ for the image signals D1, D2, . . . , Dn are changed by the same value, and it becomes possible to reconstruct a tomographic image of a different tomographic layer of the object 11.

In the aforesaid embodiment, the radiation source 10 and the sheet changer 20 are mechanically connected by the connection means 60. However, the radiation source 10 and the sheet changer 20 may be moved independently of each other by a radiation source movement means and a sheet changer movement means, and operations of the two movement means may be controlled by corresponding control signals so that the radiation source 10 and the sheet changer 20 satisfy the linear rule and the geometric rule. Also, instead of controlling the movements of the radiation source 10 and the sheet changer 20 by the controller 80, a different control means may be used for controlling the movements thereof.

Further, in order to make the read-out image signals D1, D2, ..., Dn detected from a plurality of the stimulable phosphor sheets 5 correspond to the irradiation angles $\theta$ and $\delta$, instead of storing the bar codes in conformity with the irradiation angles $\theta$ and $\delta$ in the memory 33, sheet identification codes of a different type may be stored in the memory in conformity with the irradiation angles $\theta$ and $\delta$. Also, instead of storing the sheet identification codes in the memory 33, the image recording sequence of a plurality of the stimulable phosphor sheets 5 may be made to coincide with the radiation image read-out sequence, and the information on the irradiation angles $\theta$ and $\delta$ stored in the memory 33 may be read out in the sequence in which the information is stored. In this manner, it is possible to make the irradiation angles $\theta$ and $\delta$ correspond accurately to the read-out image signals D1, D2, ..., Dn.

I claim:
1. A radiation image recording apparatus comprising:
   (i) a radiation source for emitting a radiation to an object,
   (ii) a radiation source movement means for moving said radiation source from a first position to a second position to change an irradiation angle of said radiation with respect to said object,
   (iii) a sheet changer for feeding a stimulable phosphor sheet to an image recording position exposed to said radiation passing through said object to have a radiation image of said object stored on said stimulable phosphor sheet at said image recording position, and thereafter receiving a drive signal to remove said stimulable phosphor sheet from said image recording position and feed a next stimulable phosphor sheet to said image recording position,
   (iv) a sheet changer movement means for moving the entire sheet changer from a first position to a second position where the first positions of the radiation source and the sheet changer and the second positions of the radiation source and the sheet changer are so associated with each other that the stimulable phosphor sheet at said image recording position and said radiation source at both said first and second positions of the radiation source and the sheet changer approximately satisfy the linear rule and the geometric rule with respect to a point within said object or in the vicinity thereof,
   (v) a controller for controlling operations of said sheet changer movement means and said radiation source movement means, intermittently activating said radiation source at each of said first and second positions of the radiation source and the sheet changer so that said radiation is emitted at a plurality of positions where said irradiation angles are different, and sending said drive signal to said sheet changer each time after said radiation source is activated, and
   (vi) a memory means for storing identification information on the stimulable phosphor sheet placed at said image recording position and information on said irradiation angle of said radiation emitted to said stimulable phosphor sheet so that said identification information and said information on said irradiation angle correspond to each other,
   wherein said radiation source and said sheet changer are connected to each other, and said radiation source movement means and said sheet changer movement means are constituted by a unitary movement means for moving said radiation source and said sheet changer relative to each other from their respective first positions to their respective second positions.

2. An apparatus as defined in claim 1 wherein said sheet changer comprises a first receiving section for receiving said stimulable phosphor sheets prior to exposure to said radiation, a second receiving section for receiving said stimulable phosphor sheets after exposure to said radiation, and a conveyance means for quickly conveying said unexposed stimulable phosphor sheets one by one to said image recording position and quickly conveying said exposed stimulable phosphor sheets one by one to said second receiving section.

3. An apparatus as defined in claim 2 wherein said conveyance means comprises a drive roller, guide rollers, and an endless conveyor belt applied around said drive roller and said guide rollers.

4. An apparatus as defined in claim 1 wherein said single movement means comprises a rotatable table positioned on a base, a male thread rod positioned on said rotatable table, a female thread member meshing with said male thread rod, and connection rods rotatably connected at the base ends thereof with said female thread member and connected at their opposite ends with rods for connecting said radiation source with said sheet changer.

* * * * *